US00PP36578P2

(12) United States Plant Patent
Koot

(10) Patent No.: US PP36,578 P2
(45) Date of Patent: Apr. 1, 2025

(54) ***BUDDLEJA* PLANT NAMED 'Botex 008'**

(50) Latin Name: *Buddleja davidii*
Varietal Denomination: Botex 008

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/824,902

(22) Filed: Sep. 5, 2024

(30) Foreign Application Priority Data

Sep. 13, 2023 (QZ) ..... PBR 2023/1782

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
See application file for complete search history.

*Primary Examiner* — Susan McCormick Ewoldt
(74) *Attorney, Agent, or Firm* — Penny J. Aguirre

(57) ABSTRACT

A new cultivar of *Buddleja* plant named 'Botex 008' that is characterized by its very compact, dense, and upright plant habit, its flowers that are magenta purple in color, its neat and naturally overall rounded plant shape, its very floriferous blooming habit, and its flowers that have a pleasant fragrance.

2 Drawing Sheets

Botanical classification: *Buddleja davidii*
Variety denomination: 'Botex 008'.

BACKGROUND OF THE INVENTION

The present invention relates to a new and distinct cultivar of *Buddleja davidii* will be referred to hereafter by its cultivar name, 'Botex 008'. 'Botex 008' is a new shrub grown for use as an ornamental landscape plant and as a container plant.

The new cultivar of *Buddleja* is a selection from an ongoing breeding program conducted by the Inventor in Kaatsheuvel, The Netherlands with the goal of creating new cultivars of *Buddleja* with very neat and compact plant habits combined with unique flower colors and floriferous blooming habits.

The Inventor made a cross in July of 2020 between unnamed and unpatented proprietary plants in the Inventor's breeding program; reference no. 19-016-01 as the female parent and reference no. 18-008-01 as the male parent. The Inventor selected 'Botex 008' in July of 2021 as a single unique plant amongst the seedlings that resulted from the above cross.

Asexual propagation of the new cultivar was first accomplished by the Inventor using stem cuttings in Kaatsheuvel, The Netherlands in 2021. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 008' as a unique cultivar of *Buddleja*.

1. 'Botex 008' exhibits a very compact, dense, and upright plant habit.
2. 'Botex 008' exhibits flowers that are magenta purple in color.
3. 'Botex 008' exhibits a neat and naturally overall rounded plant shape.
4. 'Botex 008' exhibits a very floriferous blooming habit.
5. 'Botex 008' exhibits flowers that have a pleasant fragrance.

The female parent of 'Botex 008' differs from 'Botex 008' in having slightly larger leaves and flowers that are pink-red in color. The male parent of 'Botex 008' differs from 'Botex 008' in having slightly smaller leaves, flowers that are blue-purple in color, smaller and shorter inflorescences, and a shorter plant height. 'Botex 008' can be compared to the *Buddleja* cultivars 'Black Knight' (not patented), 'Botex 001' and 'Botex 009'. 'Black Knight' is similar to 'Botex 006' in having flowers that are purple in color. 'Black Knight' differs from 'Botex 008' in having a taller plant height, a more open plant habit, inflorescences that are less compact and longer, and flowers that are darker purple in color. 'Botex 001' is similar to 'Botex 008' in having a naturally compact and floriferous plant habit. 'Botex 001' differs from 'Botex 008' in having flowers that are blue-violet in color. 'Botex 009' is similar to 'Botex 008' in having a very compact plant habit and a naturally rounded plant habit. 'Botex 009' differs from 'Botex 008' in having a smaller plant size and flowers that are fuschsia pink in color.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 21-cm container in Kaatsheuvel, The Netherlands.

The photograph in FIG. 1 provides a side view of the overall plant habit of 'Botex 008' in bloom.

Figure 1:
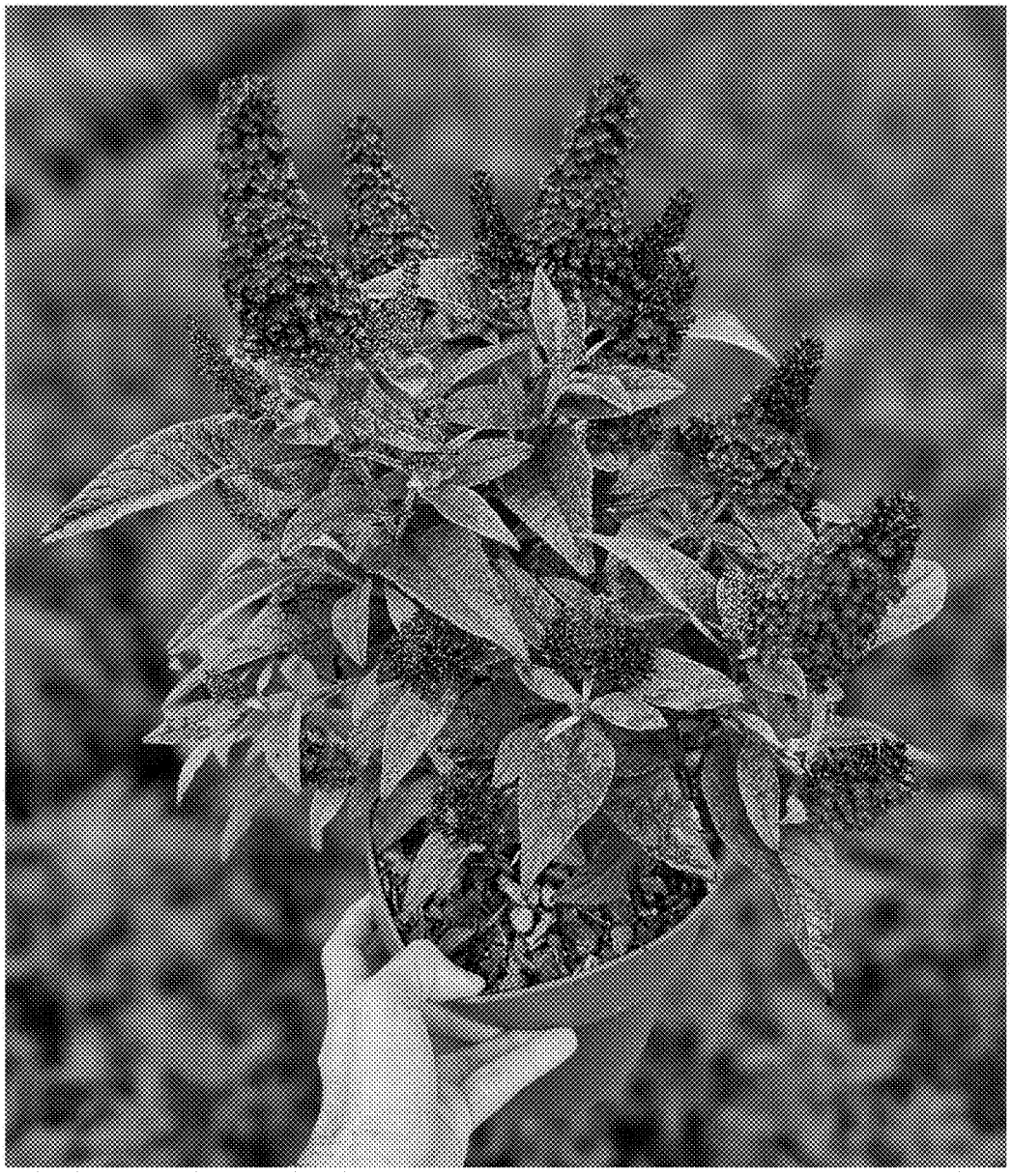
Figure 2:
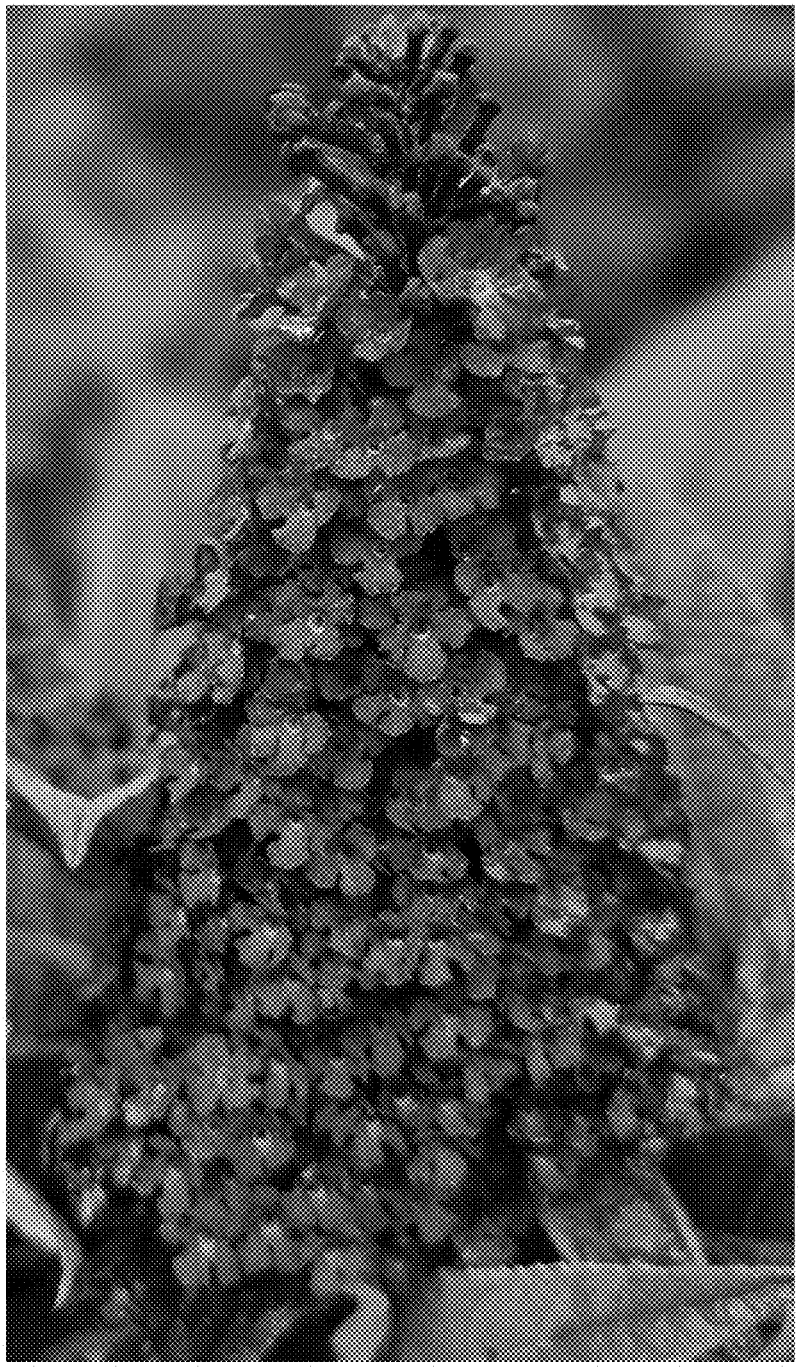

The photograph in FIG. 2 provides a close-up view of an inflorescence of 'Botex 008'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 21-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to October in The Netherlands.

*Plant type*.—Deciduous perennial shrub.

*Plant habit*.—Very compact, upright and naturally rounded, dense.

*Plant size*.—An average of 29 cm in height and 37 cm in width as a one-year-old plant in a container and reaches 80 cm in height and 80 to 90 cm in spread as grown in the landscape.

*Cold hardiness*.—At least in U.S.D.A. Zone 5.

*Diseases and pests*.—No susceptibility and resistance to diseases or pests has been observed.

*Propagation*.—Stem cuttings.

*Root description*.—Fibrous.

*Root development*.—An average of 8 weeks to initiate roots and 8 weeks to fully root as a young plant in a P9 container.

*Growth rate*.—Vigorous.

Branch description:

*Branch shape*.—Quadrangular.

*Branch color*.—Young stems; 145B, mature stems; 145A and occasional suffused with N187A, older woody stems; 199A to 199B.

*Branch strength*.—Strong.

*Branch size*.—Up to 25 cm in length and 5 mm in diameter.

*Branch surface*.—Pubescent.

*Branch aspect*.—Lateral stems held upright to an average angle of 30° to vertical.

*Branch internode length*.—Average of 3.2 cm.

*Branching*.—1 main branch, 7 secondary branches.

Foliage description:

*Leaf shape*.—Narrowly elliptical to lanceolate.

*Leaf division*.—Simple.

*Leaf base*.—Attenuate to cuneate.

*Leaf apex*.—Acute to acuminate.

*Leaf fragrance*.—None.

*Leaf venation*.—Pinnate, color; upper surface young 137C, mature 145B, lower surface young 191B, lower surface mature midrib 191B and 145B near base.

*Leaf margins*.—Serrate.

*Leaf arrangement*.—Opposite.

*Leaf attachment*.—Petiolate.

*Leaf surface*.—Both sides are smooth, matte, and pubescent.

*Leaf size*.—Up to 11 cm in length and an average of 4 cm in width.

*Leaf quantity*.—An average of 10 per stem.

*Leaf color*.—Young upper surface; 138A to 138B, young lower surface; 191C, mature upper surface; 137A, mature lower surface; 191A to 191B.

*Petioles*.—An average of 5 mm in length and 2 mm in diameter, strong, both surfaces 145A in color, surface slightly pubescent.

Inflorescence description:

*Inflorescence type*.—Compound terminal and axial panicles, held upright.

*Inflorescence size*.—An average of 6 cm in height, up to 5 cm in width (before all flowers open).

*Flower fragrance*.—Sweet, pleasant and medium strength.

*Lastingness of flowers*.—An average of 5 days, persistent.

*Flower buds*.—Oblong in shape, average of 9 mm in length and 1 mm in diameter, color; 83A, tube 77A.

*Flower aspect*.—Upright, slightly outward.

*Flower quantity*.—An average of 150 flowers per inflorescence.

*Flower type*.—Single, salverform.

*Flower surface*.—All surfaces glabrous and matte.

*Flower size*.—An average of 1.2 cm in height, 8 mm in diameter, flower throat; 4 mm in length, 1 mm in diameter, flower tube; 6 mm in length, 1.4 mm in diameter.

*Peduncles*.—An average of 2 cm in length and 2 mm in diameter, held erect, 145A in color, strong, glossy and pubescent surface.

*Pedicels*.—An average of 2 mm in length and 1 mm in diameter, held at an average angle of 45°, 145B and N187A in color, strong, surface is glossy and pubescent.

*Calyx*.—Campanulate in shape, an average of 2 mm in depth and 1.5 mm in diameter.

*Sepals*.—4, 1 whorl, rotate arrangement, fused into a campanulate shape, 3 mm in length, 1 mm in width, lanceolate in shape, acute apex, fused base, entire margin, both surfaces are matte and slightly pubescent, color; when opening and fully open upper and lower surface 145A.

*Petals*.—Average of 5, rotate, fused into salverform, 1 whorl, roughly spathulate in shape, slightly undulate margin, rounded apex, an average of 3 mm in length and 3 mm in width, outer and inner surface is glabrous and matte, color; upper and lower surface when opening and fully open; 77A, upper and lower surface older flowers; 81A with margins 83A, flower throat; 22A and 13B at base, flower tube; young and mature NN155A and 21B.

Reproductive organs:

*Gynoecium*.—1 pistil, 2 mm in length, style; an average of 1.5 mm in length, 145D in color, stigma; elongated, 1 mm in length and 145B in color, ovary is 145D in color.

*Androcoecium*.—Stamens; 4, filament; 3 mm in length and translucent in color, anther; ovate in shape, 1 mm in length, 4C in color, pollen; low in quantity, to little to measure color.

*Fruit and seed*.—No seeds or fruit observed to date.

It is claimed:

1. A new and distinct cultivar of *Buddleja* plant named 'Botex 008' as herein illustrated and described.

* * * * *